(12) United States Patent
Geist et al.

(10) Patent No.: US 10,172,597 B2
(45) Date of Patent: Jan. 8, 2019

(54) BIOPSY SYSTEMS AND METHODS

(71) Applicant: Summit Access, LLC, Englewood, CO (US)

(72) Inventors: Leroy D. Geist, Aurora, CO (US); Shawn P. Fojtik, Park City, UT (US)

( * ) Notice: Subject to any disclaimer, the term of this patent is extended or adjusted under 35 U.S.C. 154(b) by 321 days.

(21) Appl. No.: 14/932,751

(22) Filed: Nov. 4, 2015

(65) Prior Publication Data

US 2016/0120518 A1 May 5, 2016

Related U.S. Application Data

(60) Provisional application No. 62/074,754, filed on Nov. 4, 2014.

(51) Int. Cl.
*A61B 5/00* (2006.01)
*A61B 10/02* (2006.01)

(52) U.S. Cl.
CPC ...... *A61B 10/0275* (2013.01); *A61B 10/0233* (2013.01)

(58) Field of Classification Search
CPC . A61B 10/02; A61B 10/0233; A61B 10/0275; A61B 10/0291
USPC .................................................. 600/569, 572
See application file for complete search history.

(56) References Cited

U.S. PATENT DOCUMENTS

| | | | |
|---|---|---|---|
| 3,169,529 A | 2/1965 | Koenig | |
| 4,772,266 A | 9/1988 | Groshong | |
| 4,785,826 A * | 11/1988 | Ward | A61B 10/025 30/174 |
| 5,217,468 A | 6/1993 | Clement | |
| 5,267,572 A * | 12/1993 | Bucalo | A61B 10/0266 600/567 |
| 5,364,365 A | 11/1994 | Wortrich | |
| 5,385,151 A * | 1/1995 | Scarfone | A61B 10/025 600/567 |
| 5,573,008 A * | 11/1996 | Robinson | A61B 10/0266 600/567 |

(Continued)

OTHER PUBLICATIONS

United States Patent and Trademark Office Acting as The International Searching Authority, "International Search Report and Written Opinion," dated Jan. 13, 2016, in international application No. PCT/US2015/059058.

(Continued)

*Primary Examiner* — Max Hindenburg
(74) *Attorney, Agent, or Firm* — Durham Jones & Pinegar, P.C.

(57) ABSTRACT

A biopsy system is discloses that includes a percutaneous biopsy needle and an inner cannula. The percutaneous biopsy needle includes an internal passageway. At a distal end, the percutaneous biopsy needle includes an expandable section. A distal section of the internal passageway of the percutaneous biopsy needle, which corresponds to the expandable section, is tapered to enable the expandable section to expand and collapse as the inner cannula is positioned within and/or moves through the tapered distal section. The inner cannula may be configured to aspirate a sample from a location of interest within a subject's body and, in some embodiments, may cooperate with the distal end of the percutaneous biopsy needle in a manner that facilitates removal of the sample from the subject's body. Biopsy methods are also disclosed.

11 Claims, 2 Drawing Sheets

(56) References Cited

U.S. PATENT DOCUMENTS

| | | | |
|---|---|---|---|
| 5,792,074 A * | 8/1998 | Turkel | A61B 10/02 600/569 |
| 5,807,282 A * | 9/1998 | Fowler | A61B 10/0291 600/571 |
| 5,817,033 A | 10/1998 | DeSantis et al. | |
| 5,823,970 A * | 10/1998 | Terwilliger | A61B 10/0266 600/564 |
| 5,843,031 A | 12/1998 | Hermann et al. | |
| 5,885,226 A * | 3/1999 | Rubinstein | A61B 10/025 600/564 |
| 5,910,121 A * | 6/1999 | Paolo | A61B 10/025 600/562 |
| 6,176,834 B1 * | 1/2001 | Chu | A61B 10/0266 600/562 |
| 6,716,216 B1 | 4/2004 | Boucher et al. | |
| 6,758,824 B1 * | 7/2004 | Miller | A61B 10/025 600/566 |
| 7,144,386 B2 | 12/2006 | Korkor et al. | |
| 7,803,142 B2 | 9/2010 | Longson et al. | |
| 8,262,619 B2 | 9/2012 | Chebator et al. | |
| 8,764,679 B2 | 7/2014 | Miller et al. | |
| 9,282,948 B2 * | 3/2016 | Melchiorri | A61B 10/0266 |
| 9,351,710 B2 * | 5/2016 | McGhie | A61B 10/0266 |
| 2004/0030319 A1 | 2/2004 | Korkor | |
| 2005/0080430 A1 | 4/2005 | Wright, Jr. et al. | |
| 2009/0306586 A1 | 12/2009 | Ross et al. | |
| 2012/0265097 A1 | 10/2012 | Melchiorri et al. | |
| 2014/0163418 A1 | 6/2014 | Gigi | |

OTHER PUBLICATIONS

United States Patent and Trademark Office Acting as The International Searching Authority, "International Search Report and Written Opinion," dated Feb. 5, 2016, in international application No. PCT/US2015/061662.

\* cited by examiner

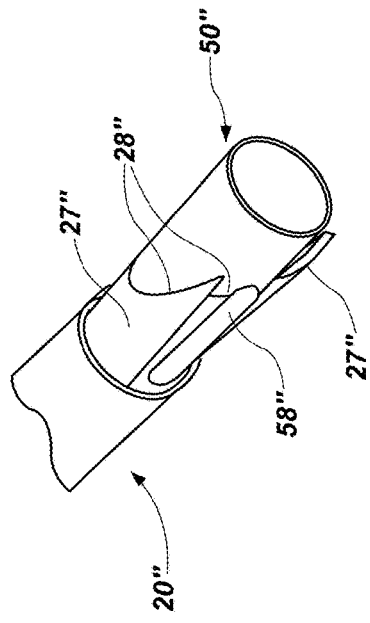
FIG. 3
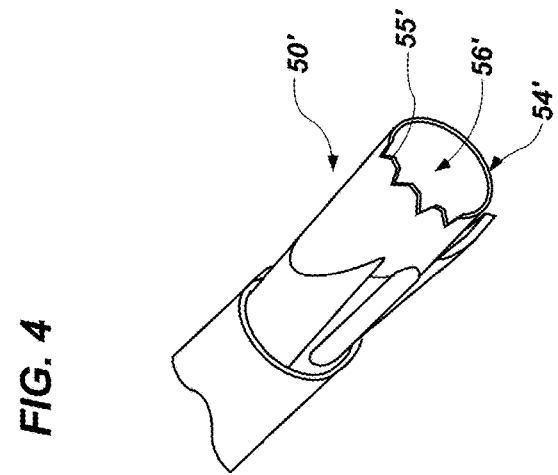
FIG. 4
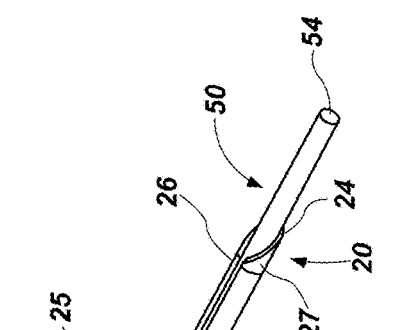
FIG. 6
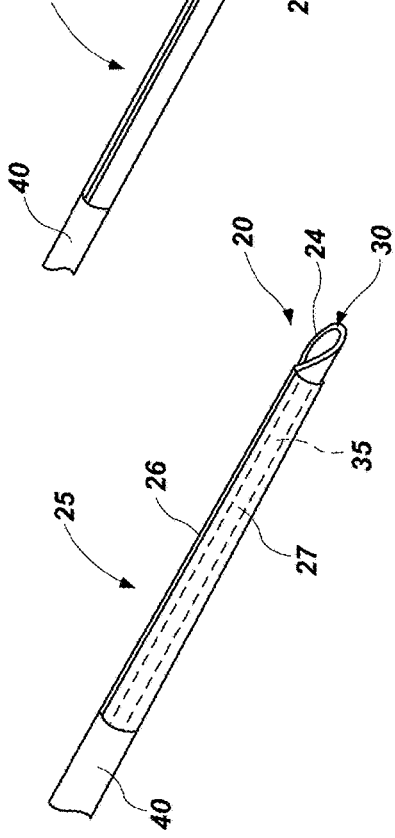
FIG. 7
FIG. 5

BIOPSY SYSTEMS AND METHODS

CROSS-REFERENCE TO RELATED APPLICATION

A claim for the benefit of priority to the Nov. 4, 2014, filing date of U.S. Provisional Patent Application No. 62/074,754, titled BIOPSY SYSTEMS AND METHODS ("the '754 Provisional Application"), is hereby made pursuant to 35 U.S.C. § 119(e). The entire disclosure of the '754 Provisional Application is hereby incorporated herein.

TECHNICAL FIELD

This disclosure relates to percutaneous biopsy needles and, more specifically, to percutaneous biopsy needles that are configured to macerate, incise and/or grasp a sample, including a tissue sample that may be of interest to a physician. Additionally, this disclosure relates to methods for using percutaneous biopsy needles.

RELATED ART

Percutaneous biopsy needles have been employed in the medical field for many years. A percutaneous biopsy needle is configured to be introduced through a subject's skin to a site of interest (e.g., the location of an abnormality, such as a subcutaneous tumor, a tumor-like lesion, etc.), from which a sample of interest may be accessed and removed, or extracted, and then subjected to histological or cellular analysis to provide a diagnosis (e.g., of the cause of the abnormality, such as cancer, etc.). Percutaneous biopsy needles are typically configured to provide access to the site of interest while minimizing the invasiveness of the procedure.

Two types of straight-needle percutaneous biopsy are currently practiced: core-needle biopsy (CNB) and fine-needle aspiration (FNA). In core-needle biopsy, a relatively large needle (e.g., an 11 gauge needle to an 18 gauge needle, etc.) is typically used with a biopsy gun to obtain a column, or "core," of tissue. During a fine needle aspiration, a very fine gauge needle (e.g., a 17 gauge needle to a 22 gauge needle, etc.) is used to aspirate a cytological sample, which may include fluid and/or cells. In either procedure, the percutaneous biopsy needle may be manually inserted through the subject's skin at a location near the site of interest. Imaging (e.g., ultrasound (U/S), computed tomography (CT), magnetic resonance imaging (MRI), etc.) may be used to may be used to direct the distal tip of the needle to the site of interest and/or to confirm that the distal tip of the needle remains at the site of interest during the procedure. With the needle in place, the sample may be extracted. In core-needle biopsy extraction may involve the use of a specialized trocar, whereas a syringe may be used to aspirate a sample from the site of interest in a fine-needle aspiration procedure.

SUMMARY

This disclosure, in various aspects, relates to enhancements to existing biopsy procedures and to alternative biopsy procedures, as well as to apparatuses that enable such enhancements and/or alternatives.

In one aspect, a percutaneous biopsy needle comprises a needle with an expandable section at its distal end and an elastomeric sheath over a proximal portion of the expandable section. The expandable section may include an external taper from a relatively large outer diameter at a proximal location to a smaller outer diameter at a more distal location, as well as an internal taper (along its internal passageway) from a relatively large inner diameter at a proximal location to a smaller inner diameter at a more distal location. Slits (e.g., laser cuts, etc.) along the length of the expandable section at various locations around the circumference of the expandable section may separate the expandable section into a plurality of expandable elements (each of which is also referred to herein as a "leaf"), and may enable expansion of the expandable section. As an elongated instrument (e.g., a wire, an inner cannula, etc.) with an outer diameter that is less than the relatively large inner diameter, but greater than the smaller inner diameter is introduced distally through the passage, the elongated instrument will force leaves of the expandable section outward, putting the expandable section into an expanded state, in which both the inner diameter and the outer diameter of the distal portion of the expandable section are effectively increased. When a portion of the elongated instrument that has forced the leaves outward is removed from the expandable section (e.g., withdrawn in a proximal direction, etc.), the leaves may be free to collapse, enabling the expandable section of the percutaneous biopsy needle to return to its initial collapsed state. The elastic sleeve around the proximal portion of the expandable section may ensure that the leaves return to their initial orientations and, thus, that the expandable section returns to its collapsed state.

In some embodiments, the portion of the internal passageway that extends through the expandable section of the percutaneous biopsy needle may be configured to completely open when the inner cannula is only partially inserted (distally) into the expandable section. In such an embodiment, the expandable section may remain completely open as the inner cannula is inserted further into the expandable section, and as the distal end of the inner cannula protrudes from the distal end of the percutaneous biopsy needle. Without limitation, the internal passageway may include one or more tapers that enable it to expand, or open, in such a way. In other embodiments, the portion of the internal passageway of the percutaneous biopsy needle that extends through the expandable section may be configured to open gradually as the distal end of the inner cannula moves therethrough, with the expandable section only opening completely when the distal end of the inner cannula is coincident with the distal end of the percutaneous biopsy needle.

In another aspect, a percutaneous biopsy needle includes an expandable section with leaves that include edges (e.g., the edges that are defined by slits between adjacent leaves, etc.) that are configured to cut into or through a sample (e.g., a tissue sample, etc.). In some embodiments, at least one edge of a leaf may be configured as a sharpened edge, or blade. Such an embodiment of percutaneous biopsy needle may be used with an inner cannula, or "opening sleeve," that includes apertures. The apertures may be elongated, and may be oriented along a length of the inner cannula. An edge of an aperture that is configured to be opposed to, or face, a sharpened edge of a leaf may also be sharpened. Tissue may be drawn (e.g., under suction, etc.) into the apertures of the inner cannula and, as the inner cannula is rotated within and relative to the expandable section of the percutaneous biopsy needle, that tissue may be cut as the aperture that holds the tissue rotates beneath the sharpened edge of a leaf. These and similar features may enable use of a percutaneous biopsy needle for maceration.

Optionally, a percutaneous biopsy needle may be used with an inner cannula that includes a sharpened, even serrated, distal end. A distal end with such a configuration may enable the inner cannula to be used to obtain a sample that comprises a column, or core, of tissue.

An embodiment of a percutaneous biopsy needle that is configured for cutting may cut as an inner cannula is rotated therein, or by rotating or oscillating (i.e., back and forth rotation of) the percutaneous biopsy needle and/or the inner cannula. Rotation of the percutaneous biopsy needle and/or in the inner cannula may include rotating a biopsy assembly of which the percutaneous biopsy needle and/or the inner cannula is/are a part, which movement may be effected manually or with an instrument (e.g., a manually operable instrument, an automated instrument, etc.) that induces rotation and/or oscillation in the biopsy assembly.

In another aspect, a biopsy system may include a percutaneous biopsy needle with an expandable section, an inner cannula, and a housing for maintaining a relationship between the inner cannula and the percutaneous biopsy needle. The housing may include a hub secured to a proximal end of the percutaneous biopsy needle, a proximal hub secured to a proximal portion of the inner cannula, and a main body to which the distal hub and the proximal hub are secured. The distal hub may be fixedly secured in place relative to a distal side of the main body. The proximal hub may be rotatably secured in place relative to a proximal side of the main body. More specifically, a retaining ring may be configured to be fixedly secured in place relative to the proximal side of the main body of the housing, while holding the proximal hub in place, and enabling the proximal hub and, thus, the inner cannula to rotate relative to the main body, the distal hub, and the percutaneous biopsy needle. In some embodiments, the proximal hub may be configured to be grasped between an individual's thumb and finger (e.g., index finger, etc.) to enable manual manipulation of the inner cannula. One or both of the retaining ring and the main body may be configured to enable or cause the proximal hub and the inner cannula to rotate and/or otherwise move relative to the main body in a controlled fashion (e.g., along a helical thread, along a spiral groove, etc.). In some embodiments, the retaining ring and/or the main body may be configured in a manner that enables the proximal hub to lock in one or more positions (e.g., in a proximal position (i.e., with the inner cannula fully withdrawn (proximally) into the percutaneous biopsy needle), in one or more intermediate positions, in a distal position (i.e., with the inner cannula fully extended (distally) from the percutaneous biopsy needle), etc.). In embodiments where the proximal hub can be locked into a distal position as the distal end of the inner cannula protrudes from the distal end of the percutaneous biopsy needle, and where the distal end of the inner cannula is blunt, the inner cannula may prevent inadvertent sticks or punctures by the distal end of the percutaneous biopsy needle when the inner cannula is fully extended and protrudes from the distal end of the percutaneous biopsy needle.

A biopsy system may also include a seal, such as an O-ring, around the inner cannula to limit fluid communication between an interior of the main body of the housing and any space between the interior of the percutaneous biopsy needle and the exterior of the inner cannula.

The proximal hub of a biopsy system may include a passage extending through its length. The passage through the proximal hub may be continuous with and, thus, communicate with a channel through the inner cannula. A proximal end of the proximal hub may be configured for coupling with another medical device in a manner that enables that medical device to communicate with the passage through the proximal hub and with the channel through the inner cannula. By way of example, and not by way of limitation, the proximal end of the proximal hub may be configured to be coupled to an aspiration device, which may apply a full or partial vacuum, or suction, to the channel of the inner cannula.

In some embodiments, a biopsy system according to this disclosure may also include an elastic sleeve around a proximal portion of the expandable section of the percutaneous biopsy needle. Other optional features of a biopsy system according to this disclosure include, but are not limited to, a cutting edge on one or more edges of one or more leaves of the percutaneous biopsy needle, one or more apertures in a distal portion of the inner cannula and/or a cutting edge at a distal end of the inner cannula.

A biopsy technique according to this disclosure may include introducing a distal end of a percutaneous biopsy needle through a subject's skin to a site of interest, at least partially expanding the expandable section of the percutaneous biopsy needle, receiving a portion of a sample or other item to be grasped within the at least partially expanded expandable section, at least partially collapsing the expandable section to grasp the sample or other item, and withdrawing the percutaneous biopsy needle, along with the sample or other item, from the body of the subject. Of course, for the at least partially expanded expandable section to at least partially receive a sample or other item, the distal end of the inner cannula should be at least partially recessed relative to, or located proximal to, the distal end of the percutaneous biopsy needle. Receipt of a sample or other item by the at least partially expanded expandable section may include applying suction to the channel of the inner cannula to draw the sample or other item at least partially into the expandable section while the expandable section is in an at least partially expanded state. Alternatively, or in addition, the distal end of the expanded expandable section may be positioned adjacent to or at least partially over the sample or other item. Withdrawal of the sample or other item and, thus, of the percutaneous biopsy needle may be effected with or without suction.

Other aspects, as well as features and advantages of various aspects, of the disclosed subject matter will become apparent to those of ordinary skill in the art through consideration of the ensuing description, the accompanying drawings and the appended claims.

BRIEF DESCRIPTION OF THE DRAWINGS

In the drawings:

FIG. 3 illustrates an embodiment of an internal passageway through an expandable section of a percutaneous biopsy needle, which includes regions with different tapers;

FIG. 4 depicts an embodiment of percutaneous biopsy needle and inner cannula that are configured to cut and aspirate;

FIGS. 5 and 6 are perspective views of an expandable section of the percutaneous biopsy needle and an elastic sleeve that surrounds a proximal portion of the expandable section, respectively showing the expandable section in collapsed and expanded states; and FIG. 7 shows an embodiment of an inner cannula that is configured to obtain a core sample from a tissue or other item of interest.

DETAILED DESCRIPTION

Figure 1:
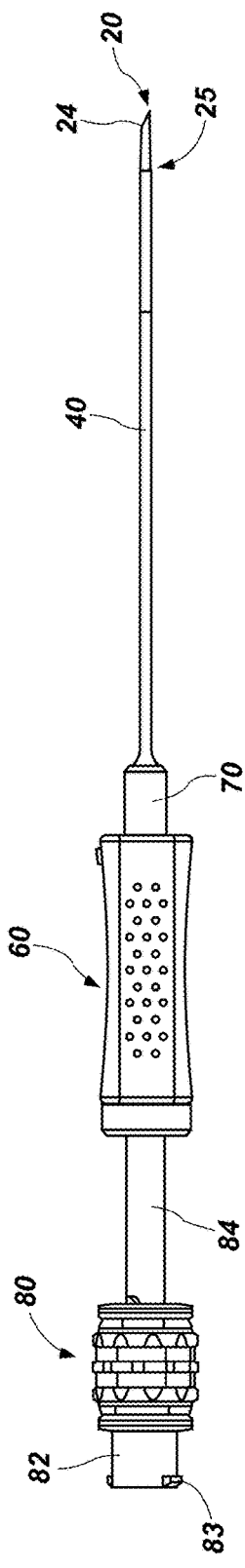
FIG. 1 is a side view of an embodiment of percutaneous biopsy system according to this disclosure.
Figure 2:
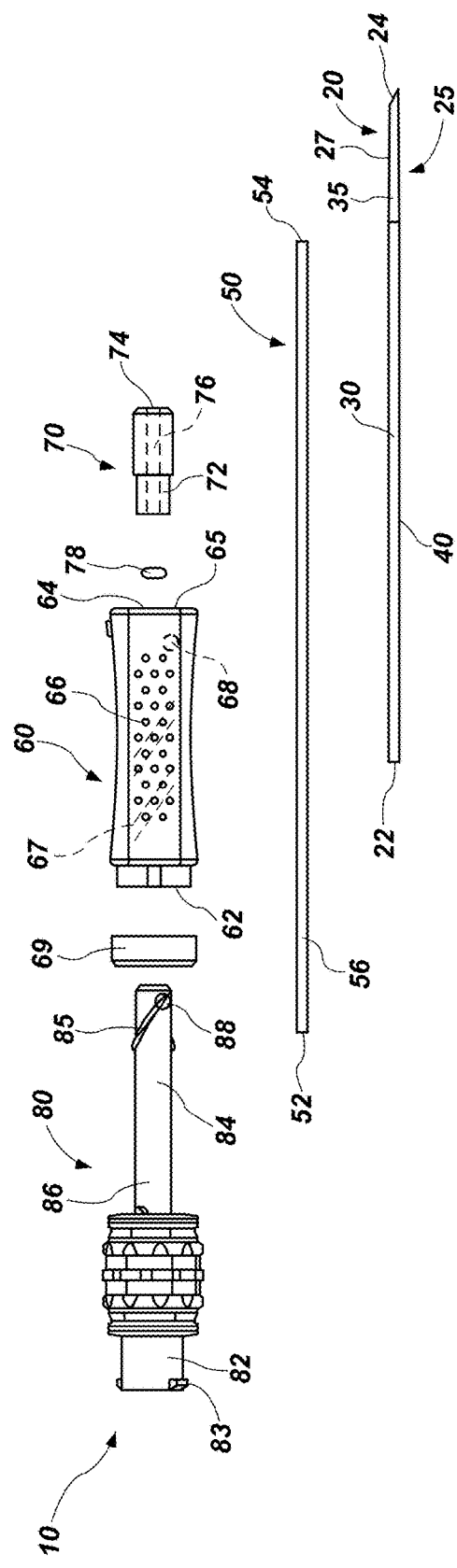
FIG. 2 is an exploded view showing various elements of the percutaneous biopsy system of FIG. 1.

With reference to FIGS. 1 and 2, an embodiment of a biopsy system 10 according to this disclosure is depicted. The biopsy system 10 includes a percutaneous biopsy needle 20, an inner cannula 50, a main body 60, a distal hub 70 and a proximal hub 80.

The percutaneous biopsy needle 20 may be configured like the micro-taper needle of U.S. Pat. No. 7,803,142, the entire disclosure of which is incorporated herein by this reference. More specifically, the percutaneous biopsy needle 20 may include a proximal end 22 and a distal end 24. An expandable section 25 may extend proximally from the distal end 24 of the percutaneous biopsy needle 20 to an intermediate location along its length. The expandable section 25 may include a plurality of slits 26 (FIGS. 3, 5 and 6) that extend through the thickness of a wall of the percutaneous biopsy needle 20, which extend along the length of the expandable section 25 and are spaced apart at different locations around the circumference of the expandable section 25. The slits 26 may separate the expandable section 25 into a plurality of expandable elements, which are also referred to herein as "leaves" 27.

In some embodiments, such as that depicted by FIGS. 1 and 2, the expandable section 25 may comprise a tapered portion of the percutaneous biopsy needle 20. More specifically, a proximal portion of the percutaneous biopsy needle 20 may have a constant outer diameter (i.e., it may be straight, or untampered), while the expandable section 25 or a portion thereof is tapered. As illustrated, an outer diameter of the percutaneous biopsy needle 20 may taper from a relatively large dimension at a proximal side of the taper (e.g. at a proximal side of the expandable section 25, etc.) to a smaller dimension at a distal side of the taper (e.g., at the distal end 24 of the percutaneous biopsy needle 20, etc.). In a specific embodiment, the relatively large dimension may be 18 gauge (0.049 inch) or larger, while the smaller dimension may be 21 gauge (0.032 inch) or smaller (e.g., 22 gauge, 25 gauge, etc.).

As illustrated by FIG. 3, an inner diameter of an expandable section 35 of an internal passageway 30, which resides within a tapered portion (e.g., the expandable section 25, etc.) of the percutaneous biopsy needle 20, may also include one or more tapers. In a specific embodiment, where the outer diameter of the percutaneous biopsy needle 20 tapers from 18 gauge to 21 gauge, the inner diameter of the corresponding expandable section 35 of its internal passageway 30 may taper from 0.039 inch to 0.022 inch. In such an embodiment, as an elongated instrument (e.g., a wire, an inner cannula 50, etc.) with an outer diameter that exceeds the inner diameter of any portion of the expandable section 35 moves distally through the internal passageway 30, the elongated instrument will force the leaves 27 outward, expanding the expandable section 25 (FIGS. 1 and 2). Expansion of the expandable section 25 includes an effective expansion of the inner diameter of the expandable section 35 of the internal passageway 30 within the expandable section 25 of the percutaneous biopsy needle 20 and an increase in the outer diameter of the expandable section 25.

In some embodiments, tapering of the expandable section 35 of the internal passageway 30 that resides within the expandable section 25 of a percutaneous biopsy needle 20 may be varied. For example, the expandable section 35 of the internal passageway 30 may include at least one tapered portion and at least one straight portion. As another example, the expandable section 35 of the internal passageway 30 may include portions with different tapers. Without limitation, FIG. 3 illustrates an embodiment in which a proximal taper 36 of the expandable section 35 of an internal passageway 30 is configured to cause the expandable section 25 (FIGS. 1 and 2) of the percutaneous biopsy needle 20 (FIGS. 1 and 2) to expand in such a way that an outer diameter of the distal end 24 (FIGS. 1 and 2) of the percutaneous biopsy needle 20 increases to a first dimension, while a distal taper 37 (which may comprise an inner diameter that decreases from a proximal side of the distal taper 37 to a distal side of the distal taper 37) of the expandable section 35 of the internal passageway 30 may enable the expanded outer diameter of the distal end 24 of the percutaneous biopsy needle 20 to remain the same while an elongated instrument continues to advance distally through the internal passageway 30. Of course, other variations in the manner in which the expandable section 35 of the internal passageway 30 through the expandable section 25 of a percutaneous biopsy needle 20 tapers, as well as variations in the outer diameter of an elongated instrument that may be moved through the expandable section 35 of the internal passageway 30, may enable the expandable section 25 of the percutaneous biopsy needle 20 to expand and/or collapse in any desired fashion as the elongated instrument moves through the internal passageway 30, or at least through the expandable section 35 of the internal passageway 30.

Turning briefly to FIG. 4, an embodiment of a percutaneous biopsy needle 20" with leaves 27" that have sharpened edges 28" is depicted. In some embodiments, the sharpened edge 28" of a leaf 27" may include serrations. As the leaves 27" of such a percutaneous biopsy needle 20" are expanded, their sharpened edges 28" are exposed, which may enable use of such a percutaneous biopsy needle 20" to cut into an obstruction or a sample (e.g., tissue, etc.) as the percutaneous biopsy needle 20" is rotated in an appropriate direction (e.g., with a sharpened edge 28" leading) or as the obstruction or sample is pulled in an appropriate direction (e.g., against the sharpened edge 28", etc.).

With returned reference to FIGS. 1 and 2, a biopsy system 10 may include an elastic sleeve 40 that surrounds at least a proximal portion of the expandable element 25 of the percutaneous biopsy needle 20. In some embodiments, the elastic sleeve 40 may extend from a location at or adjacent to the proximal end 22 of the percutaneous biopsy needle 20 to a location somewhat proximal to the distal end 24 of the percutaneous biopsy needle 20. Without limitation, a distal end of the elastic sleeve 40 may be located about 1 cm or about a quarter inch (¼ inch) proximal to the distal end 24 of the percutaneous biopsy needle 20.

The elastic sleeve 40 may be formed from a material that will enable it to conform to the shape and dimensions of the portions (e.g., a proximal portion of the expandable section 25, etc.) of the percutaneous biopsy needle 20 over which it is positioned. The material of the elastic sleeve 40, as well as its dimensions (e.g., its thickness, etc.), may enable the elastic sleeve 40 to expand while the expandable section 25 expands, and to contract upon removal of an expansion force (e.g., partial or complete removal of an elongated instrument, etc.) from the expandable section 25. As the elastic sleeve 40 contracts, it may force the leaves 27 of the expandable section 25 radially inward toward or to their original positions, thereby collapsing the expandable section 25 and, when the expansion force is totally removed therefrom, enabling the expandable section 25 to return to its collapsed state. The material from which the elastic sleeve 40 is formed, along with its dimensions, may also enable it to maintain its integrity when expanded and contracted, without significantly impeding insertion of the percutaneous biopsy needle 20 into and through a subject's skin. Suitable materials for use as the elastic sleeve 40 include, but are not limited to, dip molded elastomers and heat shrink elastomers, including elastomeric fluoropolymers. The thickness of the elastic sleeve 40 may be about 0.00025 inch to about 0.0025 inch (e.g., about 0.001 inch, etc.). FIGS. 5 and 6 respectively show an expandable section 25 of the percutaneous biopsy needle 20 in collapsed and expanded states.

As an alternative to the sleeve 40, or in addition thereto, the expandable section 25 of the percutaneous biopsy needle 20 may be formed from a material that will resiliently return to its original shape (i.e., that will enable the leaves 27 to collapse) once an expansion force (e.g., an elongated instrument, etc.) is partially or completely removed from the expandable section 25. Spring steel and nitinol are non-limiting examples of such a material.

In the embodiment of biopsy system 10 illustrated by FIGS. 1 and 2, the elongated instrument that may cause the expandable section 25 of the percutaneous biopsy needle 20 to expand may comprise an inner cannula 50. The inner cannula 50 of a biopsy system 10 according to this disclosure includes a proximal end 52 and a distal end 54. The distal end 54 may be configured to fit within the internal passageway 30 through the percutaneous biopsy needle 20 and to be moved, or translated, along a length of the internal passageway 30, including through the expandable section 35 of the internal passageway 30. In the depicted embodiment, an outer diameter of a portion of the inner cannula 50 that resides within and/or is configured to be positioned within at least a portion of the internal passageway 30 through the percutaneous biopsy needle 20—i.e., a distal portion of the inner cannula 50—is uniform. In a specific embodiment, in which the inner cannula 50 may be translated through the length of an embodiment of percutaneous biopsy needle 20 having an 18 gauge maximum outer diameter, the outer diameter of the inner cannula 50 may be 0.038 inch. As this outer diameter is greater than the minimum inner diameter of the expandable section 35 of the internal passageway 30, as depicted by FIGS. 5 and 6, introducing the distal end 54 of the inner cannula 50 into the expandable section 35 will force to the leaves 27 of the expandable section 25 of the percutaneous biopsy needle 20 radially outward, enlarging the inner diameter of the expandable section 35 of the internal passageway 30 and expanding the outer diameter of the expandable section 25 of the percutaneous biopsy needle 20, particularly at its distal end 24.

A channel 56 extends through the length of the inner cannula 50. When the inner cannula 50 is retracted (proximally), i.e., its distal end 54 is not coincident with or does not extend distally beyond the distal end 24 of the percutaneous biopsy needle 20, the channel 56 through the inner cannula 50 communicates with the internal passageway 30 through the percutaneous biopsy needle 20.

In some embodiments, the distal end 54 of the inner cannula 50 may be blunt (e.g., flat, rounded, etc.). In other embodiments, such as that depicted by FIG. 7, the distal end 54' of an inner cannula 50' may be configured to cut into a sample or another item. More specifically, the distal end 54' of such an inner cannula 50' may a sharpened edge 55', or a blade. In some embodiments, the sharpened edge 55' may include serrations, which may enable the inner cannula to cut into tissue and, thus, enable the channel 56 through the inner cannula 50 to receive a core- or column-shaped sample of the tissue.

With returned reference to FIG. 4, an inner cannula 50" may include one or more apertures 58" that, when positioned between adjacent, expanded leaves 27", are configured to enable an obstruction, tissue or another sample to be drawn therein and, as the inner cannula 50" rotates within the percutaneous biopsy needle 20", to enable the obstruction, tissue or other sample to be pulled against a sharpened edge 28" of a leaf 27" and, thus, aspirated into the channel 56" through the inner cannula 50".

Referring again to FIGS. 1 and 2, a further description of the manner in which the percutaneous biopsy needle 20 and the inner cannula 50 are assembled with one another, and a description of the manner in which the percutaneous biopsy needle 20 and the inner cannula 50 function relative to one another are provided.

A distal hub 70 may be secured to the proximal end 22 of the percutaneous biopsy needle 20 to facilitate assembly of the inner cannula 50 with the percutaneous biopsy needle 20. Specifically, the distal hub 70 may include a channel 76 that, at a distal side 74 of the distal hub 70, receives the proximal end 22 of the percutaneous biopsy needle 20. At a proximal side 72 of the distal hub 70, the channel 76 may be configured to enables alignment of the distal end 54 of the inner cannula 50 with the internal passageway 30 through the percutaneous biopsy needle 20.

An O-ring 78 may be situated at the proximal side 72 of the distal hub 70 to provide a seal between the internal passageway 30 through the percutaneous biopsy needle 20 and the outer surface of the inner cannula 50. More specifically, the O-ring 78 may surround a circumference of the inner cannula 50 and enable axial movement of the inner cannula 50 into and out of the internal passageway 30 of the percutaneous biopsy needle 20. With this arrangement, the O-ring 78 may enable pressure to be applied to channel 56 through the inner cannula 50 and to the internal passageway 30 through the percutaneous biopsy needle 20, and prevent samples that are aspirated into the channel 56 of the inner cannula 50 from leaking into other parts of the biopsy system 10.

The proximal side 72 of the distal hub 70 may also be configured to couple the percutaneous biopsy needle 20 to the main body 60 of the biopsy system 10. In a specific, but non-limiting embodiment, the proximal side 72 of the distal hub 70 may be configured to be received within an aperture 65 at a distal side 62 of the main body 60, and may be fixedly coupled to the main body 60 (e.g., mechanically, with a suitable glue or cement, etc.).

The proximal side 62 of the main body 60 is configured to receive the proximal hub 80, which, in turn, is secured to the proximal end 52 of the inner cannula 50. In a specific embodiment, the proximal end 52 of the inner cannula 50 may be fixedly secured in place (e.g., mechanically, with a suitable glue or cement, etc.) within a channel 86 through the proximal hub 80 at a distal portion 84 of the proximal hub 80 in a manner that enables communication between the channel 56 through the inner cannula 50 and the channel 86 through the proximal hub 80.

The distal portion 84 of the proximal hub 80 may be configured for receipt by a passage 66 through the main body 60 of the biopsy system 10. In the depicted embodiment, a retaining ring 69 may be configured to hold a distal-most end of the distal portion 84 of the proximal hub 80 in place within the passage 66 through the main body 60.

In some embodiments, features 85 (e.g., one or more spiral protrusions, or threads, etc.) on an outer circumference of the distal portion 84 may cooperate with (e.g., be received by, etc.) cooperating features 67 (e.g., one or more spiral grooves, etc.) on an inner circumference of the passage 66 through the main body. With such an arrangement, the movement of the distal portion 84 of the proximal hub 80 and, thus, the movement of the inner cannula 50 into and out of the percutaneous biopsy needle 20, may be controlled (e.g., by rotation of the proximal hub 80 relative to the main body 60, etc.).

In some embodiments, the distal portion 84 of the proximal hub 80, the retaining ring 69 and/or the passage 66 through the main body 60 may include one or more features 88, 68 that enable the proximal hub 80 to lock (rotationally and axially) in one or more positions (e.g., in a proximal position (i.e., with the inner cannula fully withdrawn (proximally) into the percutaneous biopsy needle 20), in one or more intermediate positions, in a distal position (i.e., with the inner cannula 50 fully extended (distally) from the percutaneous biopsy needle 20), etc.).

On its proximal side 82, the proximal hub 80 may include one or more coupling features 83 configured to enable the biopsy system 10 to be secured to another apparatus. Without limitation, the coupling features 83 may comprise luer lock elements or other features that will enable the proximal hub 80 to be coupled to and uncoupled from another apparatus, such as an aspiration device.

From the foregoing, various uses of the biopsy system 10, as disclosed above, should be apparent to those of ordinary skill in the art.

Although the foregoing description sets forth many specifics, these should not be construed as limiting the scope of any of the claims, but merely as providing illustrations of some embodiments and variations of elements or features of the disclosed subject matter. Other embodiments of the disclosed subject matter may be devised which do not depart from the spirit or scope of any of the claims. Features from different embodiments may be employed in combination. Accordingly, the scope of each claim is limited only by its plain language and the legal equivalents thereto.

What is claimed:

1. A biopsy system, comprising:
    a percutaneous biopsy needle with an internal passageway extending through a length thereof, the internal passageway including a tapered section within an expandable section at a distal portion of the percutaneous biopsy needle, the expandable section including a plurality of leaves that are circumferentially adjacent to one another and that are configured to be forced radially outward from one another;
    an inner cannula configured to move coaxially through the internal passageway through the percutaneous biopsy needle, a distal portion of the inner cannula configured to force the plurality of leaves of the expandable section radially outward as the distal portion of the inner cannula is positioned within the tapered section of the internal passageway; and
    an elastic sleeve over a proximal portion of the expandable section, the elastic sleeve configured to cause the plurality of leaves to collapse upon removal of the distal portion of the inner cannula from the tapered section of the internal passageway through the percutaneous biopsy needle.

2. The biopsy system of claim 1, wherein at least one leaf of the plurality of leaves includes a sharpened edge.

3. The biopsy system of claim 2, wherein at least one slot extends through the distal portion of the inner cannula, the at least one slot being configured to receive a sample and to pull the sample across the sharpened edge of the at least one leaf as the inner cannula rotates within the internal passageway of the percutaneous biopsy needle.

4. The biopsy system of claim 1, wherein a distal end of the inner cannula is sharpened to enable the distal end to obtain a core sample.

5. The biopsy system of claim 1, wherein the housing is configured to lock the inner cannula into place in at least one position along the length of the percutaneous biopsy needle.

6. The biopsy system of claim 5, wherein the housing is configured to lock the inner cannula into place in a distal-most position, in which a distal end of the inner cannula protrudes beyond a distal end of the percutaneous biopsy needle.

7. A biopsy system, comprising:
    a percutaneous biopsy needle with an internal passageway extending through a length thereof, the internal passageway including a tapered section within an expandable section at a distal portion of the percutaneous biopsy needle, the tapered section including a plurality of different tapers, the expandable section including a plurality of leaves that are circumferentially adjacent to one another and that are configured to be forced radially outward from one another; and
    an inner cannula configured to move coaxially through the internal passageway through the percutaneous biopsy needle, a distal portion of the inner cannula configured to force the plurality of leaves of the expandable section radially outward as the distal portion of the inner cannula is positioned within the tapered section of the internal passageway, the plurality of different tapers controlling expansion and/or collapsing of the plurality of leaves of the expandable section as the distal portion of the inner cannula moves through the tapered section.

8. The biopsy system of claim 7, wherein at least one leaf of the plurality of leaves includes a sharpened edge.

9. The biopsy system of claim 8, wherein at least one slot extends through the distal portion of the inner cannula, the at least one slot being configured to receive a sample and to pull the sample across the sharpened edge of the at least one leaf as the inner cannula rotates within the internal passageway of the percutaneous biopsy needle.

10. The biopsy system of claim 7, wherein a distal end of the inner cannula is sharpened to enable the distal end to obtain a core sample.

11. The biopsy system of claim 7, wherein the housing is configured to lock the inner cannula into place in at least one position along the length of the percutaneous biopsy needle.

* * * * *